(12) United States Patent
Krieger et al.

(10) Patent No.: US 10,588,637 B2
(45) Date of Patent: Mar. 17, 2020

(54) TEMPORARY OCCLUSION OF BLOOD VESSEL USING EXTRA-LUMINAL BALLOON

(71) Applicant: Cook Medical Technologies LLC, Bloomington, IN (US)

(72) Inventors: Joshua F. Krieger, Topsfield, MA (US); Rebecca Roeder, Bloomington, IN (US); Paul Gagne, Darien, CT (US)

(73) Assignee: Cook Medical Technologies LLC, Bloomington, IN (US)

( * ) Notice: Subject to any disclaimer, the term of this patent is extended or adjusted under 35 U.S.C. 154(b) by 286 days.

(21) Appl. No.: 15/484,464

(22) Filed: Apr. 11, 2017

(65) Prior Publication Data

US 2017/0333048 A1    Nov. 23, 2017

Related U.S. Application Data

(60) Provisional application No. 62/337,578, filed on May 17, 2016.

(51) Int. Cl.
*A61B 17/12*  (2006.01)
*A61M 25/10*  (2013.01)
(Continued)

(52) U.S. Cl.
CPC .. *A61B 17/12136* (2013.01); *A61B 17/00491* (2013.01); *A61B 17/1204* (2013.01); *A61B 17/12013* (2013.01); *A61B 17/12109* (2013.01); *A61B 17/12186* (2013.01); *A61M 25/10* (2013.01); *A61M 25/104* (2013.01); *A61B 2017/00778* (2013.01); *A61B 2017/1205* (2013.01); *A61M 25/1002* (2013.01); *A61M 2025/1052* (2013.01); *A61M 2025/1081* (2013.01); *G09B 23/285* (2013.01); *G09B 23/30* (2013.01)

(58) Field of Classification Search
CPC .... A61B 2017/00778; A61B 17/12136; A61B 17/00
USPC ........................................................ 604/509
See application file for complete search history.

(56) References Cited

U.S. PATENT DOCUMENTS 4,800,879 A    1/1989    Golyakhovsky et al.
5,222,970 A    6/1993    Reeves
(Continued)

FOREIGN PATENT DOCUMENTS

WO    03073944    9/2003

OTHER PUBLICATIONS

European Patent Office, European Search Report for Application No. 17171335.7 Published Jan. 25, 2018, Munich Germany.

*Primary Examiner* — Nathan R Price
*Assistant Examiner* — John A Doubrava
(74) *Attorney, Agent, or Firm* — Liell & McNeil

(57) ABSTRACT

A method of treating a vessel, such as sclerotherapy, includes moving a short balloon catheter to a position at which a compliant extra-luminal balloon is outside of the vessel at an occlusion site, and between the vessel and a non-compliant bearing surface. The vessel is occluded at the occlusion site by inflating the compliant extra-luminal balloon of the balloon catheter, and bearing an outer surface of the balloon against the vessel and the non-compliant bearing surface. The vessel is medically treated upstream from the occlusion site. The short balloon catheter includes a wire guide lumen.

11 Claims, 3 Drawing Sheets

(51) Int. Cl.
    *A61B 17/00*     (2006.01)
    *G09B 23/28*     (2006.01)
    *G09B 23/30*     (2006.01)

(56) References Cited

U.S. PATENT DOCUMENTS

| | | | |
|---|---|---|---|
| 5,236,437 A * | 8/1993 | Wilk | A61B 17/22032 604/908 |
| 5,639,274 A | 6/1997 | Fischell et al. | |
| 5,868,707 A | 2/1999 | Williams et al. | |
| 5,964,730 A | 10/1999 | Williams et al. | |
| 7,175,646 B2 | 2/2007 | Brenneman et al. | |
| 7,276,037 B2 | 10/2007 | Ravikumar | |
| 8,449,483 B2 | 5/2013 | Eddy | |
| 2006/0276749 A1* | 12/2006 | Selmon | A61B 6/12 604/164.01 |
| 2008/0215031 A1 | 9/2008 | Belfort et al. | |
| 2008/0300571 A1 | 12/2008 | LePivert | |
| 2009/0222003 A1* | 9/2009 | Otley | A61B 17/12 606/41 |
| 2011/0226647 A1 | 9/2011 | Lentz | |
| 2013/0072957 A1* | 3/2013 | Anderson | A61M 25/104 606/194 |
| 2014/0228876 A1* | 8/2014 | Copeta | A61M 25/0194 606/194 |
| 2016/0058983 A1* | 3/2016 | Poker | A61L 29/16 604/509 |

* cited by examiner

TEMPORARY OCCLUSION OF BLOOD VESSEL USING EXTRA-LUMINAL BALLOON

TECHNICAL FIELD

The present disclosure relates generally to temporary occlusion of blood vessels with an extra-luminal balloon, and more particularly to temporary closure of a vein while medically treating the vein upstream from the occlusion site.

BACKGROUND

Foam and glue schelrotherapy are used commonly to ablate the great saphenous or other large superficial veins or perforators in the legs. The technique has shown good efficacy, but is not without risk. The largest risk to the patient is embolic particles or generated thrombus moving into the deep system and either creating conditions for deep vein thrombosis, directly causing pulmonary embolism, or even causing a transient eschemic attack or stroke from cerebral artery embolization.

The present disclosure is directed toward reducing this risk and for other procedures that could benefit from temporary non-destructive occlusion of a blood vessel.

SUMMARY

In one aspect, a medical device assembly includes a short balloon catheter with a shaft that is less than 20 centimeters long. The short balloon catheter defines a wire guide lumen and includes a compliant extra-luminal balloon mounted about a distal segment of the shaft. A wire guide is positioned in the wire guide lumen. A sheath that is about a same length as the short balloon catheter receives the short balloon catheter so that the compliant extra-luminal balloon is covered by the sheath.

In another aspect, a method of treating a vessel includes moving a short balloon catheter to a position at which a compliant extra-luminal balloon is outside of a vessel at an occlusion site, and between the vessel and a non-compliant bearing surface. The vessel is occluded at the occlusion site by inflating the compliant extra-luminal balloon, and bearing an outer surface of the balloon against the vessel and the non-compliant bearing surface. The vessel is then medically treated upstream from the occlusion site.

DETAILED DESCRIPTION

Figure 1:
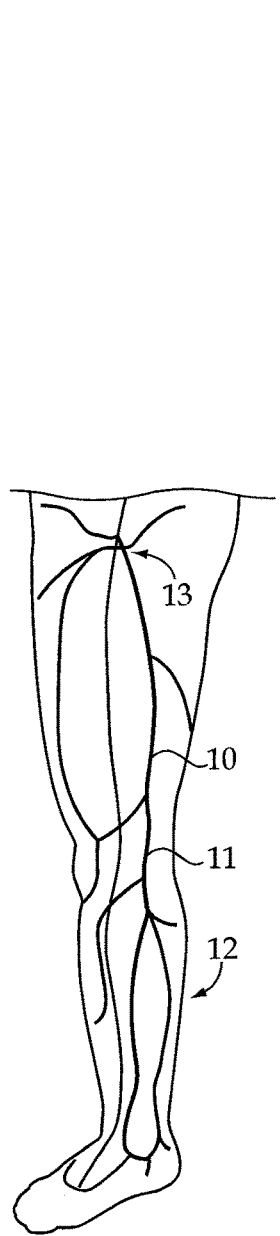
FIG. 1 is a side schematic view of a patient's leg with a vein to be medically treated.

In order to mitigate the risk of embolic particles or generated thrombus moving into the deep system when performing foam or glue sclerotherapy, the present disclosure teaches the use of a distal protection device. In particular, and in reference to FIG. 1, a patient's leg 12 has a number of vessels 10 that include a great saphenous vein 11 to be treated with foam or glue sclerotherapy. A distal protection strategy may include blocking the great saphenous vein at an occlusion site 13, where the greater saphenous vein traverses the deep fascia to confluence with the deep veins, while the sclerotherapy is performed upstream from the occlusion site 13. The present disclosure teaches temporarily occluding the vein 11 at the occlusion site 13 using a compliant balloon to temporarily provide an extra-vascular occlusion, which can protect the patient during the sclerotherapy procedure occurring upstream from the occlusion site 13. The great saphenous vein 11 runs through a fascial sheath before perforating at a saphenous opening through a fascial layer, which is defined by the superficial and deep fascia, immediately before joining the femoral vein of the deep system. The fascial sheath has low compliance. Those skilled in the art will appreciate that the fascial sheath is often accessed during vein ablation procedures in order to introduce tumescent anesthesia, or in the course of sclerotherapy or glue closure to access the vein. As access is already common to the procedure, the present disclosure proposes using the same access technique to place a wire guide and subsequently a compliant balloon to bear against the outer surface of the saphenous vein and rely upon the fascia to support the balloon to squeeze the vein closed.

Figure 2:
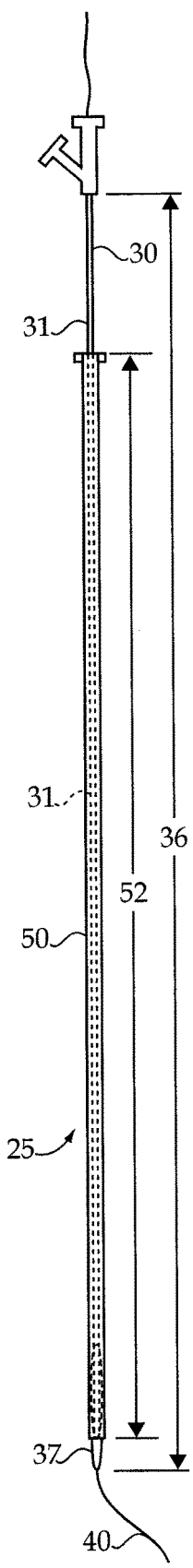
FIG. 2 is a side view of a medical device assembly according to one aspect of the present disclosure.
Figure 3:
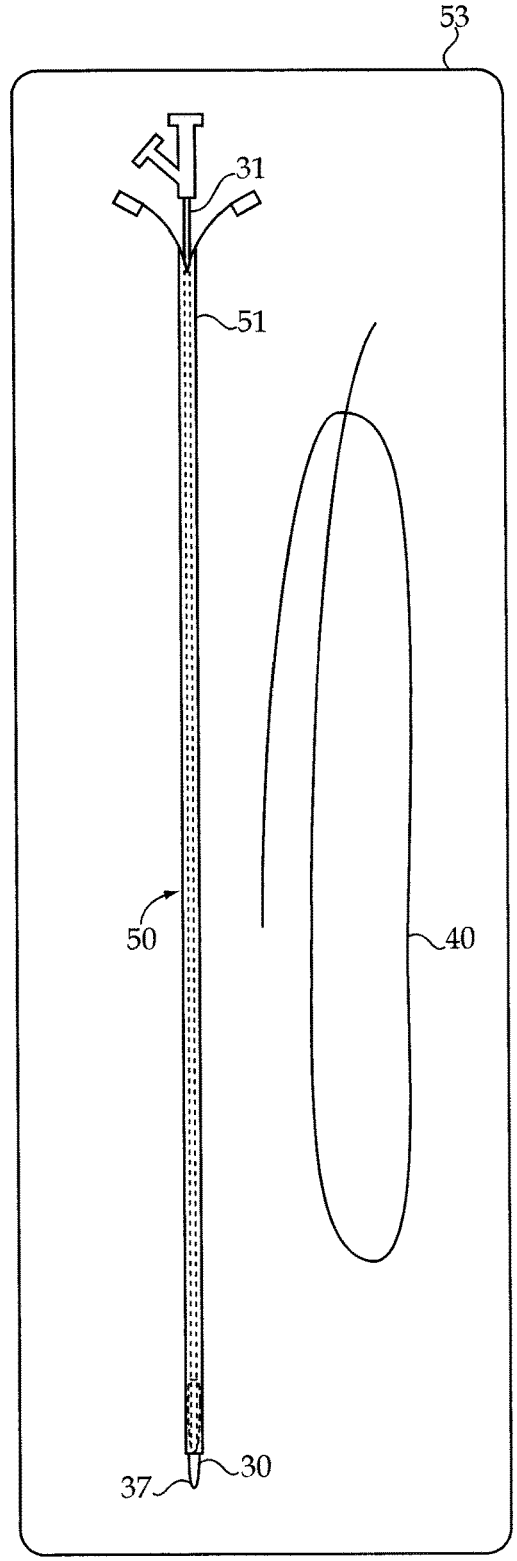
FIG. 3 is a schematic view of a medical kit that includes a medical device assembly according to another aspect of the present disclosure.
Figure 4:
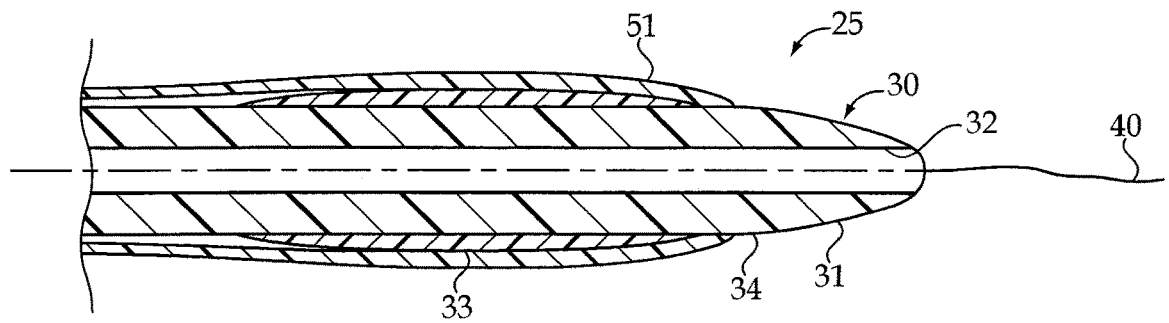
FIG. 4 is a partial side schematic view of a distal segment of a medical device assembly according to the present disclosure.

Referring now in addition to FIGS. 2-4, a medical device assembly 25 for use in temporary extra-vascular occlusion according to the present disclosure includes a short balloon catheter 30 that includes a shaft 31 that is less than 20 centimeters long and defines a wire guide lumen 32. A compliant extra-luminal balloon 33 is mounted about a distal segment 34 of the shaft 31. The relatively short length 36 of ballooned catheter 30 is indicative of the expected short distance between the access point in the patient's leg 12 and the occlusion site 13, which may be located in any suitable location, such as along the fascial sheath that encloses a segment of the saphenous vein 11 or at an edge where the fascial sheath opens, such as the saphenous opening just upstream of the connection to the femoral vein, or other thigh and calf perforator veins. A wire guide 40 is positioned in wire guide lumen 32 when the short balloon catheter 30 is being maneuvered to occlusion site 13. The short balloon 30 is received in a sheath 50 to cover the compliant extra-luminal balloon 33 while the medical device assembly 25 is being maneuvered to the occlusion site 13. The sheath 50 has a length 52 that is about a same length 36 as the short balloon catheter 30. In the context of the present disclosure, the term "about" means that when the ratio of the two lengths is rounded to a whole number, the whole number is the numeral 1. The embodiment of FIG. 3 differs from that of FIG. 2 in that wire guide 40 is not yet positioned in short balloon catheter 30 and the sheath 50 is a peal away sheath 51 of a type well known in the art. In the case of the medical device assembly 25 using the peal away sheath 51, the peal away sheath 51 would be pealed away after the balloon is positioned at the occlusion site location 13, preferably without moving the balloon. After the peal away sheath is removed, the balloon would be inflated. In the embodiment shown in FIG. 2 the thin sheath 50 may be utilized over the entire catheter shaft 31 minus approximately 2 centimeters or so at the proximal hub or manifold. Once the balloon is correctly located, the sheath 50 would be retracted over the balloon catheter shaft 31 without moving the balloon 33. The exposed balloon would then be inflated at the occlusion site 13.

INDUSTRIAL APPLICABILITY

The present disclosure finds general applicability where there is a need or desire to temporarily occlude a blood vessel by pinching the vessel from the outside using a compliant balloon. The present disclosure finds specific application to temporarily occluding veins at an occlusion site downstream from a location where the vein is being medically treated. Finally, the present disclosure finds specific application to blocking the great saphenous vein while performing foam and glue sclerotherapy upstream from the occlusion site. Although the disclosure shows one occlusion site 13 at a fascial perforator, those skilled in the art will recognize that other fascial perforator sites and fascial sheaths in the body could also be used as occlusion sites.

Figure 5:
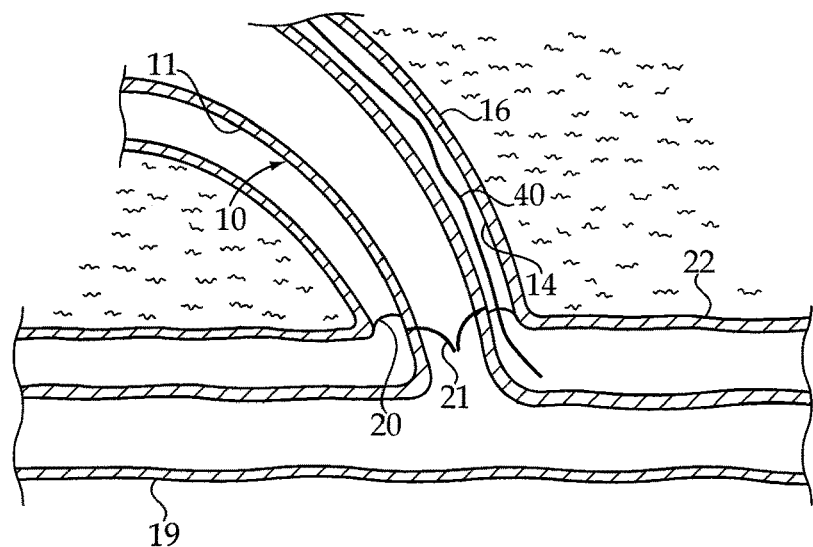
FIG. 5 is a side sectioned schematic view of a wire guide positioned through a saphenous perforation in the fascial sheath.
Figure 6:
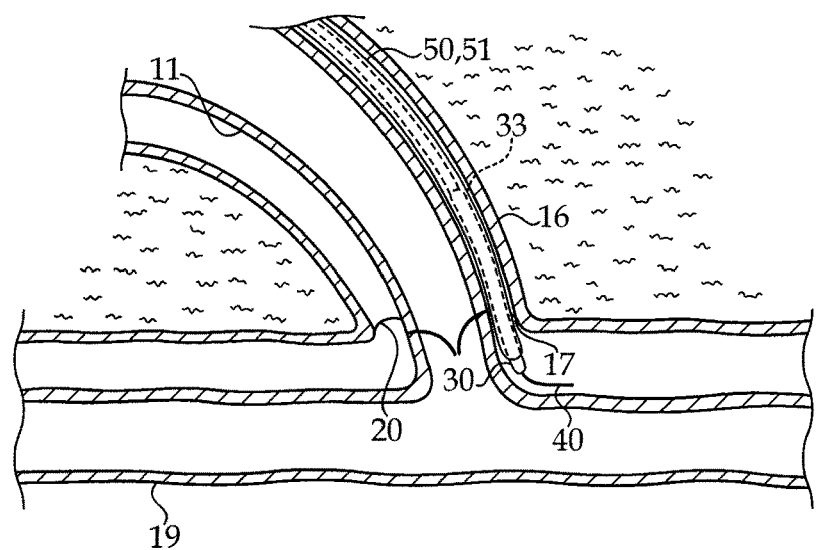
FIG. 6 is a view similar to FIG. 5 after a medical device assembly according to the present disclosure has been positioned at an occlusion site.
Figure 7:
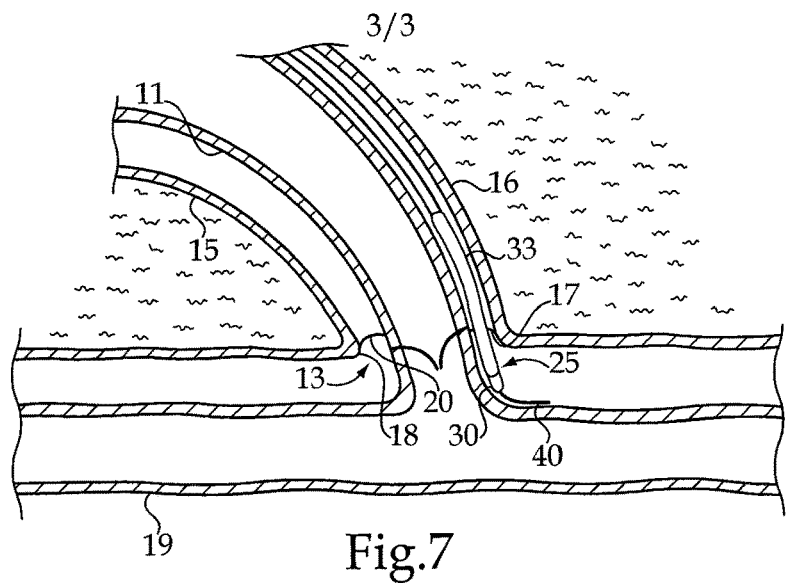
FIG. 7 is a view similar to FIG. 6 after the sheath has been moved to expose the compliant extra-luminal balloon.
Figure 8:
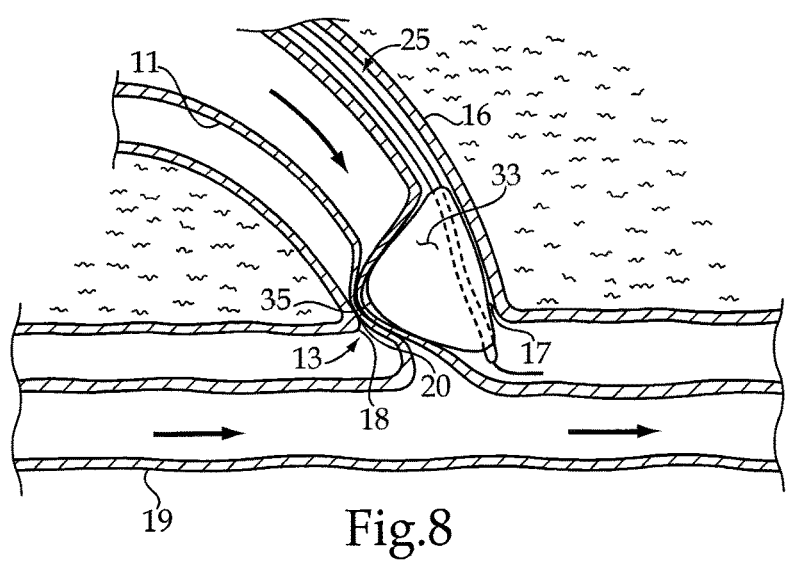
FIG. 8 is a view similar to FIG. 7 after a compliant extra-luminal balloon has been inflated to temporarily occlude the great saphenous vein at the saphenous perforation through the fascial sheath.
Figure 9:
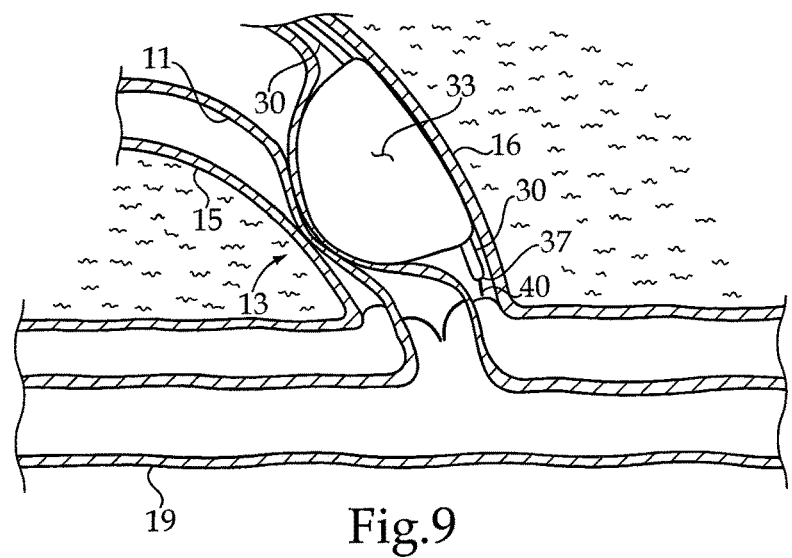
FIG. 9 is a view similar to FIG. 8 except showing the occlusion site within the fascial sheath.

In order to perform a method according to the present disclosure, several standard techniques may be utilized, which need not be taught again here. For instance, ultrasound may be utilized as guidance and confirmation at all steps. The method can be initiated by placing a needle (not shown) into the fascial sheath 16 in the space between fascia 15/16 and vein 11, as shown in FIG. 5. Next, the physician may place a small wire guide (may have a hook on end for stability), such as a 0.018 inch wire guide in to hold in place while the needle is removed. Next, the physician may dilate up with a micro-puncture kit (not shown) and place a larger wire in place for holding, such as a 0.035 inch wire guide 40, which may have a hook on its end for stability. The short balloon catheter is then moved along the wire guide 40 to a position at which the balloon 33 is outside of the vessel 11 at occlusion site 13, and the balloon 33 is positioned between the vessel 11 and a non-compliant bearing surface 14, which is fascia 15 in the illustrations of FIGS. 5-9. As best shown in FIG. 8, the balloon presses against the vein 11, causing the vein 11 to be temporarily occluded at the point of balloon 33. The pressure and dimensions of the balloon can be measured and may be modified in order to achieve closure of the vein, without creating undue stress or discomfort to the patient. For instance, this strategy may be well suited for use in sclerotherapy or glue closure of both the great saphenous vein, or perforator veins between the superficial and deep venous systems. In the case of perforator veins, this protection could be used for sclerotherapy or glue closure of the perforator veins themselves, or the connected superficial system at sites in the lower half of the thigh and the entire calf. Thus, FIG. 8 shows the balloon being inflated at an edge 17 in the perforation 18 at the saphenous opening 20. FIG. 9 differs in that the balloon 33 is shown being inflated within the facial sheath 16. In such a case, the balloon is constrained by the fascial sheath 16 and would press against the outer surface of the vein, causing the vein to be temporarily occluded at the occlusion site 13 where the balloon 33 is trapped between the fascial sheath 16 and the saphenous vein 11. Those skilled in the art will appreciate that the pressure and dimensions of the balloon 33 can be measured and modified in order to achieve closure of the vein, without creating undue stress and/or discomfort to a patient. Thus, the vessel 11 is occluded at the occlusion site 13 by inflating the compliant extra-luminal balloon 33 of the balloon catheter 30. The outer surface 35 of the compliant extra-luminal balloon 33 bears against the outer surface of vein 11 and the non-compliant bearing surface 14, which may be fascia 15 or the fascial sheath 16. While the vein is temporarily occluded, the physician may medically treat the vein upstream from the occlusion site 13. This medical treatment may, for instance, include sclerotherapy or application of glue. Prior to performing the medical procedure, the physician may verify temporary cessation of flow in the vein 11 using doppler ultrasound in a manner well known in the art. After the medical procedure is performed, and cessation of flow in the vein 11 is no longer needed, the balloon 33 may be deflated and the entire medical device assembly 25 including wire guide 40 may be removed from the patient. Those skilled in the art will appreciate that pressure does not need to be held, as no vessel has been pierced.

The sheath 50, 51 may be used to cover the compliant extra-luminal balloon 33 while the medical device assembly 25 is maneuvered to the occlusion site 13. The compliant extra-luminal balloon may be uncovered prior to inflation by moving the sheath 50, 51 relative to the short balloon catheter 30. In the case of the embodiment shown in FIG. 2, this may be accomplished by sliding sheath 50 in the proximal direction toward the hub of the sheath to uncover balloon 33. In the case of the embodiment shown in FIG. 3, the sheath 51 may be moved by being pealed away while maintaining the balloon catheter 30 in place in a manner well known in the art.

The present description is for illustrative purposes only, and should not be construed to limit the breadth of the present disclosure in any way. Thus, those skilled in the art will appreciate that various modifications might be made to the presently disclosed embodiments without departing from the full and fair scope and spirit of the present disclosure. For instance, a non-compliant bearing surface according to the present disclosure need not necessarily be fascia, other "soft" tissue may be sufficiently non-compliant to facilitate closure of a vessel. Other aspects, features and advantages will be apparent upon an examination of the attached drawings and appended claims.

What is claimed is:

1. A method of treating a vessel, comprising the steps of:
   moving a balloon catheter to a position at which a compliant extra-luminal balloon is outside of a vessel at an occlusion site, and between an exterior side of the vessel and a non-compliant bearing surface;
   occluding the vessel at the occlusion site by inflating the compliant extra-luminal balloon of the balloon catheter, and bearing an outer surface of the compliant extra-luminal balloon against the exterior side of the vessel and the non-compliant bearing surface;
   medically treating the vessel upstream from the occlusion site.

2. The method of claim 1 wherein the step of medically treating includes performing sclerotherapy on the vessel.

3. The method of claim 1 wherein the vessel is a vein; and the non-compliant bearing surface is fascia.

4. The method of claim 1 wherein the moving step includes guiding the balloon catheter to the occlusion site with a wire guide.

5. The method of claim 2 including deflating the compliant extra-luminal balloon and moving the balloon catheter away from the occlusion site after completing the sclerotherapy on the vessel.

6. The method of claim 3 wherein the vein is a leg vein.

7. The method of claim 3 wherein the non-compliant bearing surface is a fascial sheath.

8. The method of claim 3 wherein the non-compliant bearing surface is an edge of a perforation through a deep fascia.

9. The method of claim 6 wherein the leg vein includes a saphenous vein.

10. The method of claim 4 including covering the compliant extra-luminal balloon with a sheath during the moving step; and uncovering the compliant extra-luminal balloon prior to the inflating step by moving the sheath relative to the balloon catheter.

11. The method of claim 10 including peeling the sheath away from the balloon catheter.

\* \* \* \* \*